United States Patent
Sievert et al.

(10) Patent No.: US 7,348,446 B2
(45) Date of Patent: Mar. 25, 2008

(54) PROCESS FOR THE PRODUCTION OF TRIALKYLSILYL(FLUOROSULFONYL)DIFLUOROACETATE

(75) Inventors: Allen Capron Sievert, Elkton, MD (US); Lee G. Sprague, Augusta, GA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/799,417

(22) Filed: May 1, 2007

(65) Prior Publication Data

US 2007/0270602 A1    Nov. 22, 2007

Related U.S. Application Data

(60) Provisional application No. 60/801,567, filed on May 18, 2006.

(51) Int. Cl.
*C07F 7/04* (2006.01)
(52) U.S. Cl. ..................................... 556/428
(58) Field of Classification Search .............. None
See application file for complete search history.

(56) References Cited

U.S. PATENT DOCUMENTS 5,268,511 A    12/1993    Farnham

FOREIGN PATENT DOCUMENTS

WO    WO 93/20085    10/1993

OTHER PUBLICATIONS

William R. Dolbier Jr., et al. "Trimethylsilyl fluorosulfonyldifluoroacetate (TFDA): a new, highly efficient difluorocarbene reagent", Journal of Fluorine Chemistry, 125 (2004) pp. 459-469.
Robin J. Terjeson et al., "Silver (Fluorosulfonyl)Difluoroacetate—A New Route to Fluorosulfonyl Esters", Journal of Fluorine Chemistry, 42 (1989) pp. 187-200.
Feng Tian et al., "A Novel and Highly Efficient Synthesis of gem-Difluorocyclopropanes", Organic Letters, vol. 2, No. 4, (2000) pp. 563-564.
W. R. Dolbier, Jr., et al., "Preparation and Use of a New Difluorocarbene Reagent, Trimethylsilyl 2-Fluorosulfonyl-2,2-Difluoroacetate: n-Butyl 2,2-Difluorocyclopropanecarboxylate", Organic Syntheses, p. 172, vol. 80, (2003).
J. D. Citron, "Reactions of Group IVB Compounds with Acyl Fluorides", Journal of Organometallic Chemistry, pp. 21-26, vol. 30, (1971).

*Primary Examiner*—Samuel A. Barts

(57) ABSTRACT

A process for the production of trialkylsilyl (fluorosulfonyl) difluoroacetate by contacting (fluorosulfonyl)difluoroacetyl fluoride with siloxane. The amount of (fluorosulfonyl)difluoroacetic acid by-product in trialkylsilyl(fluorosulfonyl) difluoroacetate is reduced by contacting said mixture with trialkylsilyl halide.

21 Claims, No Drawings

PROCESS FOR THE PRODUCTION OF TRIALKYLSILYL(FLUOROSULFONYL) DIFLUOROACETATE

BACKGROUND OF THE INVENTION

1. Field of the Invention

This invention relates to a process for the production of trialkylsilyl (fluorosulfonyl)difluoroacetate by contacting (fluorosulfonyl)difluoroacetyl fluoride with siloxanes, preferably in the absence of carboxylate anion silylation catalyst. This invention further relates to reducing the amount of (fluorosulfonyl)difluoroacetic acid in the trialkylsilyl (fluorosulfonyl)difluoroacetate by contacting with trialkylsilyl halide.

2. Description of Related Art

Trialkylsilyl(fluorosulfonyl)difluoroacetate ($FSO_2CF_2CO_2SiR_3$, referred to herein as RSUTAS) is a precursor of difluorocarbene and is used for the cyclopropanation of olefins (see Dolbier, et al. in Journal of Fluorine Chemistry, Volume 125, pages 459 to 469 (2004)). This cyclopropanation has value in the pharmaceutical and agricultural chemical industries as a means for preparing commercially useful compounds.

Trimethylsilyl(fluorosulfonyl)difluoroacetate (RSUTMS) was originally prepared by the reaction of the silver salt of (fluorosulfonyl)difluoroacetic acid with trimethylsilyl iodide (Terjeson et al. in J. Fluorine Chem., Volume 42, pages 187 to 200 (1989)).

Tian et al. in Organic Letters, Volume 2, pages 563 to 564 (2000) describe a procedure for preparation of RSUTMS involving the reaction of (fluorosulfonyl)difluoroacetic acid (RSUA) with trimethylsilyl chloride. RSUTMS manufacturing procedures based on RSUA are not preferred because RSUA is derived from (fluorosulfonyl)difluoroacetyl fluoride (RSU). Thus, when RSU (acid fluoride) is hydrolyzed to make RSUA (the acid), hydrogen fluoride (HF) is generated and must be disposed of. Then, when RSUA is reacted with trialkylsilyl halide (halotrialkylsilane), for example the chloride, hydrogen chloride is generated. Thus, this process generates stoichiometric quantities of HF and HCl.

Another problem with known methods for the production of RSUTAS is that the product is usually contaminated with (fluorosulfonyl)difluoroacetic acid ($FSO_2CF_2CO_2H$, RSUA) as a by-product due to reaction of the RSU precursor and/or the trialkylsilyl ester product with adventitious water. The presence of RSUA in RSUTAS is deleterious to subsequent uses of this compound as a cyclopropanation reagent. The literature describes addition of triethylamine to RSUTMS to remove RSUA. Unfortunately, this procedure is difficult to control and can result in rapid decomposition of the entire sample.

Farnham in U.S. Pat. No. 5,268,511 teaches the preparation of trifluorovinyl ethers by reaction of a siloxane with hexafluoropropylene oxide-based carboxylic acid fluorides or anhydrides, optionally in the presence of a carboxylate anion silylation catalyst to provide useful reaction rates. The resulting silyl ester intermediate is converted to the trifluorovinyl ether by heating in the presence of a thermolysis catalyst. However, disclosure of Farnham is limited to carboxylic acid fluorides as a starting material which contain the group $—O(C_2F_4)COF$ or $—O(C_2F_4)—C(O)O(O)C(C_2F_4)O—$ and thus exclude RSU as a starting material. As discussed above, RSUTAS decomposes to form a difluorocarbene radical and cannot form a vinyl ether. Moreover, if it is attempted to produce RSUTAS employing a process step as in Farnham, i.e., reacting siloxane with RSU in the presence of carboxylate anion silylation catalyst, RSUTAS is not produced in significant yield.

A process is needed to make RSUTAS which reduces or eliminates the significant production of unwanted by-products such as HF. In addition, it is desirable to reduce the RSUA by-product.

BRIEF SUMMARY OF THE INVENTION

In accordance with the invention, it has been discovered that trialkylsilyl(fluorosulfonyl)difluoroacetate (RSUTAS) is produced by contacting (fluorosulfonyl)difluoroacetyl fluoride (RSU) with siloxane. The process provides RSUTAS without the significant production of unwanted by-products such as HF. In a preferred form of the invention, the process is carried out in the absence of carboxylate anion silylation catalyst Surprisingly, in the absence of catalyst, the process of the invention provides good conversions and yields at good reaction rates.

In accordance with another aspect of the invention, the amount of (fluorosulfonyl)difluoroacetic acid (RSUA) byproduct in the RSUTAS product is reduced by contacting the mixture of RSUTAS and RSUA with a trialkylsilyl halide. This is advantageously carried out in one embodiment of the invention concurrently with the reaction of RSU and siloxane or, in another embodiment of the invention, concurrently with or after the distillation step in which RSUTAS is recovered.

In one preferred embodiment of the invention, a process is provided for the production of trimethylsilyl(fluorosulfonyl)difluoroacetate (RSUTMS), comprising: (a) contacting (fluorosulfonyl)difluoroacetyl fluoride (RSU) with hexamethyldisiloxane (HMDS) to produce a mixture comprising trimethylsilyl(fluorosulfonyl)difluoroacetate and (fluorosulfonyl)difluoroacetic acid; (b) distilling said mixture to form a distillate comprising trimethylsilyl(fluorosulfonyl)difluoroacetate (RSUTMS) and (fluorosulfonyl)difluoroacetic acid (RSUA); (c) contacting said distillate with trimethylsilyl chloride to convert at least a portion of said (fluorosulfonyl)difluoroacetic acid (RSUA) therein to trimethylsilyl (fluorosulfonyl)difluoroacetate (RSUTMS), and (d) recovering trimethylsilyl (fluorosulfonyl)difluoroacetate (RSUTMS).

In another preferred embodiment the invention, a process is provided for the production of trimethylsilyl(fluorosulfonyl)difluoroacetate, comprising: (a) contacting (fluorosulfonyl)difluoroacetyl fluoride with hexamethyldisiloxane to produce a mixture comprising trimethylsilyl (fluorosulfonyl)difluoroacetate and (fluorosulfonyl)difluoroacetic acid; (b) distilling said mixture in the presence of trimethylsilyl chloride to form a distillate comprising trimethylsilyl(fluorosulfonyl)difluoroacetate; and (c) recovering trimethylsilyl (fluorosulfonyl)difluoroacetate.

DETAILED DESCRIPTION OF THE INVENTION

The present invention provides a process for the production of trialkylsilyl(fluorosulfonyl)difluoroacetate (RSUTAS), comprising contacting (fluorosulfonyl)difluoroacetyl fluoride (RSU) with siloxane.

Siloxanes used in accordance with the present invention are compounds containing the grouping Si—O—Si with each of the three free bonds to silicon bound to a hydrocarbyl, substituted hydrocarbyl, or oxysilyl group. By an oxysilyl group is meant the O—Si group in which the free valences of the silicon can be bound to a hydrocarbyl or substituted hydrocarbyl group. Siloxanes can contain either one siloxane group, as in hexamethyldisiloxane, can be cyclic compounds and contain several siloxane groups, as in octamethylcyclotetrasiloxane, or can contain many siloxane groups as in poly(dimethylsiloxane). Useful siloxanes include, but are not limited to, hexamethyldisiloxane, hexaethyldisiloxane, hexamethylcyclotrisiloxane, octamethylcyclotetrasiloxane, 1,3-diethyl-1,1,3,3-tetramethyldisiloxane and poly(dimethylsiloxane). Preferred siloxanes are compounds of the formula $R_3SiOSiR_3$, wherein each R is independently $C_1$-$C_3$ hydrocarbyl. More preferred siloxanes are hexamethyldisiloxane (HMDS) and hexaethyldisiloxane (HEDS). Most preferred is HMDS. Reaction proceeds faster with HMDS, probably because of reduced steric hindrance compared to the larger ethyl group on HEDS.

In accordance with a preferred form of the invention, contacting of RSU with siloxane is carried out in the absence of carboxylate anion silylation catalyst. By "absence of carboxylate anion silylation catalyst" is meant that catalysts of the type described by Farnham in U.S. Pat. No. 5,268,511 are not added. The catalysts of Farnham are described as sources of carboxylate anion, —$O(C_2F_4)CO_2$—, which can be a carboxylate anion itself (added as a salt) or sources which in the process can react with acyl fluorides or carboxylic anhydrides to form the carboxylate anion including silanoates, fluoride, and carboxylates such as acetate and perfluorooctanoate. Although Farnham does not disclose RSU, "absence of carboxylate anion silylation catalyst" in this application also means that sources of carboxylate anions corresponding to RSU, e.g., salts of RSUA, are not added. If it is attempted to use the carboxylate anion catalysts as in Farnham in the process of the invention, the product RSUTAS is not formed in significant yield. This is believed to be due to reactions of the catalyst with the RSUTAS product.

In accordance with a more preferred form of the invention, contacting of RSU with siloxane is carried out in the absence of silylation catalyst. By absence of silylation catalyst is meant that no material or treatment is added during the contacting step that increases the reaction rate by reducing the activation energy of the silylation process. It is understood that although surfaces that are unavoidably present in any reaction vessel may have incidental catalytic or anticatalytic effects on the silylation process, it is believed such effect makes an insignificant contribution, if any, to the silylation reaction rate. More specifically, absence of silylation catalyst means absence of an added catalyst that is known from other reactions to promote the silylation of an acid fluoride and formation of a silyl ester, including the carboxylate anion silylation catalysts discussed above. Surprisingly, without a catalyst as in preferred forms of the invention, the process provides good conversions and yields at good reaction rates.

The amount of siloxane contacted with RSU is preferably about 0.9 to about 1.5 moles of Si—O—Si bond in the siloxane per mole of RSU. Generally, the amount of siloxane contacted with RSU can be close to equimolar. For example, in the case of one embodiment of the invention employing the reaction of HMDS with RSU, the preferred mole ratio is about 1:1. Amounts of siloxane in excess of the stochiometric ratio may be preferred if it is desired to totally consume all of the RSU. Amounts of RSU in excess of the stoichiometric ratio may be preferred if it is desired to totally consume all of the siloxane. In the latter embodiment of the present invention, the subsequent isolation of the silyl ester RSUTAS by distillation is simplified by the absence of siloxane when the siloxane has a boiling point closer to that of RSUTAS than that of RSU.

Contacting of RSU with siloxane can be done in the liquid phase. RSUTAS (the reaction product) can serve as a reaction solvent, as can an excess of one of the reactants, RSU or siloxane. However, it is preferred that the contacting of RSU with siloxane is carried out in the liquid phase in the absence of any other added solvent other than reactants or products.

Contacting of RSU with siloxane is preferably done at a temperature of from about 50° C. to about 130° C., more preferably from about 90° C. to about 120° C. The autogenous pressure of the reaction contents at the reaction temperature is advantageously used to carry out the reaction. Contact times are typically from about one hour to eighteen hours. It is surprising that RSU is converted to RSUTAS so quickly and in such good conversion and yield without the use of catalyst.

The reactor, its feed lines, effluent lines, and associated units should be constructed of materials resistant to carboxylic acid fluorides such as RSU, and to hydrogen fluoride. Typical materials of construction include stainless steels, in particular of the austenitic type, the well-known high nickel alloys, such as Monel® nickel-copper alloys, Hastelloy® nickel-based alloys and, Inconel® nickel-chromium alloys, and copper-clad steel.

In one embodiment of the present process, reactants RSU and siloxane are added to the reactor. The reactor is sealed and the contents are heated to the desired temperature for a time sufficient to cause substantial conversion of RSU to RSUTAS. This mode of operation is known as batch mode.

In another embodiment of the present process, the reactor is charged with the siloxane, and RSU is added to the siloxane at the desired reaction temperature over a period of one to eighteen hours. This mode of operation is known as semi-batch mode.

In another embodiment of the semi-batch mode, the reactor is charged with RSU, and the siloxane is added to the RSU at the desired reaction temperature over a period of one to eighteen hours.

After a time suitable to convert the RSU to RSUTAS, the reaction mixture is preferably cooled and RSUTAS can be recovered. Preferably, distillation is used to recover RSUTAS. The distillation may be carried out initially at atmospheric pressure to remove low-boiling reaction components such as excess RSU (if present) and fluorosilane co-product which typically is formed in the process, e.g., fluorotrimethylsilane when the siloxane is HMDS. The pressure of the distillation is then reduced to distill the RSUTAS. Preferred distillation pressures are in the range of 1 to 50 mm Hg (0.13 to 6.7 kPa). It is preferred that the temperature of the distillation pot not exceed about 160° C. so as to avoid thermal decomposition of the product RSUTAS.

The primary side reaction in synthesis of RSUTAS is the hydrolysis of RSU or of RSUTAS by adventitious water. In the synthesis of RSUTMS ($FSO_2CF_2CO_2Si(CH_3)_3$) the acid contaminant is (fluorosulfonyl)difluoroacetic acid ($FSO_2CF_2CO_2H$, RSUA). In another aspect of the present invention, the RSUA content of RSUTAS is reduced by contacting with trialkylsilyl halide. In one preferred form of the invention, the contacting occurs concurrently with the contacting of RSU with siloxane In another form of the invention, the contacting follows contacting of RSU with siloxane, in the same, or different reaction vessel. In another preferred form of the invention, the contacting of the mixture of RSUTAS containing RSUA with trialkylsilyl halide occurs during, or after the distillation step.

In one possible mode of operation of the present process, the product mixture comprising the RSUTAS, RSUA, fluorosilane co-product, and any unreacted siloxane or RSU starting material are distilled under vacuum. The recovered RSUTAS and any RSUA by-product are then contacted with trialkylsilyl halide and the resulting mixture re-distilled under vacuum. Specifically, in the preparation of RSUTMS by reaction of HMDS with RSU, the product mixture comprises, RSUTMS, RSUA, fluorotrimethylsilane, and any unreacted HMDS or RSU. The reaction mixture is distilled to remove unreacted RSU and fluorotrimethylsilane co-product. The remainder of the product comprising RSUTMS, RSUA, and any unreacted HMDS is then contacted with trimethylsilyl halide. After a time sufficient to reduce the concentration of RSUA, this mixture is then distilled to recover RSUTMS.

In a preferred mode of operation of the present process, the product mixture comprising RSUTAS, RSUA, fluorosilane co-product and any unreacted siloxane or acid fluoride starting materials is contacted with trialkylsilyl halide in a vessel that may be same or different than the reaction vessel. The resulting mixture is then distilled under vacuum to recover the silyl ester.

The trialkylsilyl halides suitable for converting RSUA by-product to the RSUTAS preferably comprise compounds of the formula $R_3SiX$, wherein each R is independently $C_1$-$C_3$ hydrocarbyl and X is a halide selected from the group consisting of chlorine, bromine, and iodine. When trimethylsilyl esters are being produced, the preferred trialkylsilyl halide is trimethylsilyl chloride. When triethylsilyl esters are being produced, the preferred trialkylsilyl halide is triethylsilyl chloride. Some hydrogen halide is produced by these reactions but substantially all exits the reaction mixture as a gas.

The amount of trialkylsilyl halide contacted with RSUA containing RSUTAS is preferably about 1 to about 5 moles of trialkylsilyl halide per mole of RSUA. Typically, an excess of the trialkylsilyl halide is employed. Contacting of a mixture comprising RSUTAS with RSUA with trialkylsilyl halide is preferably carried out in the liquid phase in the absence of added solvent at a temperature of from about 25° C. to about 140° C. and at the autogenous pressure of the mixture at the reaction temperature. The mixture comprising the RSUTAS and RSUA is combined with trialkylsilyl halide and then brought to the preferred temperature. Alternatively, either component may be added to the other component over time in a measured fashion at the reaction temperature. Excess unreacted trialkylsilyl halide may be recovered and reused.

RSUTMS that is recovered by the preferred process of this invention employing contacting with trialkylsilyl halide is preferably substantially free of RSUA. By substantially free is meant RSUTAS containing less than about 3 mole % RSUA, preferably less than about 1 mole % RSUA.

As a typical example of the efficacy of this preferred form of the present process, the amount of RSUA in a mixture of RSUTAS and RSUA can be reduced from about 9 mole % to about 1 mole % (see Example 1).

One embodiment of the present invention thus provides a process for the production of RSUTMS, comprising: (a) contacting RSU with hexamethyldisiloxane to produce a mixture comprising RSUTMS and RSUA; (b) distilling said mixture to form a distillate comprising RSUTMS and RSUA; (c) contacting said distillate with trimethylsilyl chloride to convert RSUA therein to RSUTMS, and (d) recovering RSUTMS.

Another embodiment of the present invention thus provides a process for the production of RSUTMS, comprising: (a) contacting RSU with hexamethyldisiloxane to produce a mixture comprising RSUTMS and RSUA; (b) distilling said mixture in the presence of trimethylsilyl chloride to form a distillate comprising RSUTMS; and (c) recovering RSUTMS.

EXAMPLES

In the examples the following abbreviations are used:

RSU: (fluorosulfonyl)difluoroacetyl fluoride, $FSO_2CF_2C(O)F$

RSUA: (fluorosulfonyl)difluoroacetic acid, $FSO_2CF_2CO_2H$

RSUTMS: trimethylsilyl(fluorosulfonyl)difluoroacetate, $FSO_2CF_2CO_2Si(CH_3)_3$, reaction product.

FTMS: Fluorotrimethylsilane, reaction product.

HMDS: Hexamethyldisiloxane, reactant.

CTMS: Chlorotrimethylsilane, reactant.

Example 1

Preparation of RSUTMS

A 600 ml autoclave is cooled in ice water, evacuated, and charged with hexamethyldisiloxane (294 ml, 220 g, 1.36 moles) and RSU (255.3 g, 1.42 moles). The autoclave is then heated at 100° C. for 18 hours; the pressure rises to a maximum of 100 psig (0.79 MPa). The reaction mixture is cooled to room temperature and a black liquid (471.4 g) is removed from the autoclave.

The product above, and another prepared in substantially the same manner, are combined in a 2 L flask and distilled using a water-cooled condenser and a dry ice trap between the vacuum source and distillation apparatus to trap co-product trimethylsilyl fluoride. Results of the distillation are summarized in Table 1.

TABLE 1

| Fraction No. | Head Temp (° C.) | Pressure (mm Hg) | Weight (g) |
|---|---|---|---|
| Dry ice trap | — | — | 254.3 |
| 1 | 23–40 | 760 | 6.9 |
| 2 | 24–65 | 25 | 157.6 |
| 3 | 65–67 | 25 | 488.4 |
| Heel | — | — | 5.8 |

Fractions 2 and 3 are RSUTMS containing 8.4 mole % RSUA. Yield of RSUTMS is 86.9% based on HMDS, the limiting reagent, which is substantially all converted in the course of the reaction.

Reducing the Amount of RSUA in RSUTMS

A 500 ml three neck flask fitted with a condenser, thermometer, and addition funnel is charged with 40.0 g of CTMS. The addition funnel, is charged with 100.0 grams of RSUTMS (containing about 9 mole % RSUA). The flask contents are refluxed and the RSUTMS is added over the course of about 2.2 hours as the temperature of the flask contents is increased to 81.5° C. After the addition of RSUTMS is complete, the flask is allowed to cool with stirring for two hours. Analysis of the reaction mixture by $^{19}$F NMR indicated that the concentration of RSUA had decreased from about 9 mole % to about 1 mole %.

Example 2

Preparation of RSUTMS

In this Example, trimethylsilyl chloride is included in the initial charge to the reactor, to reduce the RSUA in the product RSUTMS.

A 210 ml Hastelloy™ C shaker tube is charged with hexamethyldisiloxane (28.3 g, 0.174 mole) and CTMS (2.8 g, 0.0258 mole). The tube sealed, cooled in dry ice, evacuated, and charged with RSU (33 g, 0.183 mole). The tube is then heated at 105° C. for 6 hours; the pressure rose to a maximum of 67 psig (0.56 MPa). The reaction mixture is cooled to room temperature and the yellow-brown liquid product transferred to a flask set for distillation. Analysis of the crude product by $^1$H NMR shows that conversion is about 93% (based on the limiting reactant, hexamethyldisiloxane). Analysis of the reaction mixture by $^{19}$F NMR indicates that the concentration of RSUA relative to RSUTMS is about 8.6 mole %. Low-boiling components (RSU and fluorotrimethylsilane) are distilled at atmospheric pressure up to a pot temperature of 103° C. The RSUTMS is then distilled at 34 mm Hg (4.5 kPa) to give 34.6 grams (0.138 mol) of product containing about 2 mole % RSUA. This is an 84% yield of distilled product in the six hour reaction time. The lower RSUA content as compared to that found in Example 1 before the CTMS treatment, shows the effectiveness of the addition of trimethylsilyl chloride at the start of the reaction.

Example 3

Preparation of RSUTMS

A one liter autoclave is charged with hexamethyldisiloxane (243.5 g, 1.50 moles) and then purged with nitrogen, cooled, and evacuated. RSU (286 g, 1.59 moles) is then added at 1.9° C. The autoclave is then heated to 100.6° C. over the course of about one hour with 600 rpm agitation; the pressure rises to a maximum of 69 psig (0.58 MPa). The reaction is stirred at 100° C. for six hours and then cooled to room temperature. The crude product (521 g) is removed from the autoclave; the concentration of RSUA relative to RSUTMS is about 7.7 mole %. $^1$H NMR shows HMDS conversion to be about 97%.

The product is transferred to a 500 mL flask fitted with a vacuum-jacketed Vigreux column and a cold finger distillation head. Volatile components (RSU and fluorotrimethylsilane) are removed from the mixture by distillation at atmospheric pressure up to a pot temperature of 127.6° C. The pot is allowed to cool to room temperature and then CTMS (41.7 g, 0.384 mole) is added to the pot. The flask is then heated at atmospheric pressure to a maximum of 107.8° C. as excess CTMS distilled overhead. The pressure in the distillation is then reduced and RSUTMS is recovered. The heart cut (320.6 g) contains about 3.3 mole % RSUA. Yield of RSUTMS is 85% based on HMDS converted in the six hour reaction time.

Example 4

Preparation of RSUTMS

Following the procedure of Example 3, RSU (428 g, 2.38 moles) is contacted with HMDS (361.8, 2.25 moles) for 6 hr at 95° C. After discharge, $^1$H NMR analysis of the crude product indicates the presence of 0.20 mole % HMDS, 48.1 mole % FTMS, and 51.7 mole % RSUTMS; the conversion of HMDS is about 99.6%. $^{19}$F NMR analysis of the crude product indicates that the relative amount of RSUA to RSUTMS is about 3.0 mole %. The crude products from this reaction and another carried out in substantially the same manner (but with a reaction temperature of 110° C.) are combined (1558 g total) and distilled at atmospheric pressure to remove low-boiling components. Chlorotrimethylsilane (126.04 g) is added to the distillation pot and the mixture stirred overnight and then distilled at a pressure of about 370 to 380 mbar (37 to 38 kPa). The pressure of the distillation is then reduced to 33-36 mbar (3,3-3.6 kPa). After a small fore-run (59 g), the product (1008 g; 87.7% yield based on HMDS charged) is collected at head temperature of 59.3 to 61.3° C. at a pressure of 33 to 36 mbar (3.3 to 3.6 kPa). The RSUA content of the product is mole 1.4 mole %.

What is claimed is:

1. A process for the production of trialkylsilyl (fluorosulfonyl)difluoroacetate, comprising contacting (fluorosulfonyl)difluoroacetyl fluoride with siloxane.

2. The process of claim 1 wherein said contacting is carried out in the absence of carboxylate anion silylation catalyst.

3. The process of claim 1 wherein said siloxane is at least one compound selected from the group consisting of hexamethyldisiloxane, hexaethyldisiloxane, hexamethylcyclotrisiloxane, octamethylcyclotetrasiloxane, 1,3-diethyl-1,1,3,3-tetramethyldisiloxane and poly(dimethylsiloxane).

4. The process of claim 1 wherein said siloxane is at least one compound selected from the group consisting of hexamethyldisiloxane and hexaethyldisiloxane.

5. The process of claim 1 wherein said siloxane is hexamethyldisiloxane.

6. The process of claim 1 wherein the amount of said siloxane contacted with (fluorosulfonyl)difluoroacetyl fluoride is from about 0.90 to about 1.5 moles of siloxane per mole of (fluorosulfonyl)difluoroacetyl fluoride.

7. The process of claim 1 wherein said contacting is carried out in the liquid phase with trialkylsilyl(fluorosulfonyl)difluoroacetate serving as a solvent.

8. The process of claim 7 wherein said contacting is carried out in the liquid phase in the absence of added solvent.

9. The process of claim 1 wherein said contacting is carried out at a temperature of from about 50° C. to about 130° C.

10. The process of claim 1 wherein said contacting produces a mixture of trialkylsilyl(fluorosulfonyl)difluoroacetate and (fluorosulfonyl)difluoroacetic acid.

11. The process of claim 10 further comprising contacting said mixture of trialkylsilyl(fluorosulfonyl)difluoroacetate and (fluorosulfonyl)difluoroacetic acid with trialkylsilyl halide, wherein said halide is selected from the group consisting of bromine, chlorine and iodine.

12. The process of claim 11 wherein said contacting of said mixture of trialkylsilyl(fluorosulfonyl)difluoroacetate and (fluorosulfonyl)difluoroacetic acid with said trialklysilyl halide is concurrent with said contacting of said (fluorosulfonyl)difluoroacetyl fluoride with said siloxane.

13. The process of claim 11 further comprising recovering said mixture of trialkylsilyl(fluorosulfonyl)difluoroacetate and (fluorosulfonyl)difluoroacetic acid by distillation.

14. The process of claim 13 wherein said contacting of said mixture of trialkylsilyl(fluorosulfonyl)difluoroacetate and (fluorosulfonyl)difluoroacetic acid with said trialklysilyl halide is concurrent with or after said distillation.

15. The process of claim 11 wherein said trialkylsilyl halide is trimethylsilyl chloride.

16. The process of claim 11 wherein the amount of said trimethylsilyl halide contacted with said mixture of trialkylsilyl (fluorosulfonyl)difluoroacetate and (fluorosulfonyl)difluoroacetic acid is from about 1 to about 5 moles of trimethylsilyl halide per mole of (fluorosulfonyl)difluoroacetic acid.

17. The process of claim 11 wherein the amount of said (fluorosulfonyl)difluoroacetic acid in said mixture of trialkylsilyl (fluorosulfonyl)difluoroacetate and (fluorosulfonyl)difluoroacetic acid following said contacting is less than about 3 mole percent.

18. A process for the production of trimethylsilyl (fluorosulfonyl)difluoroacetate, comprising: (a) contacting (fluorosulfonyl)difluoroacetyl fluoride with hexamethyldisiloxane to produce a mixture comprising trimethylsilyl (fluorosulfonyl)difluoroacetate and (fluorosulfonyl)difluoroacetic acid; (b) distilling said mixture to form a distillate comprising trimethylsilyl(fluorosulfonyl)difluoroacetate and (fluorosulfonyl)difluoroacetic acid; (c) contacting said distillate with trimethylsilyl chloride under conditions sufficient to convert at least a portion of said (fluorosulfonyl)difluoroacetic acid therein to trimethylsilyl (fluorosulfonyl)difluoroacetate, and (d) recovering trimethylsilyl (fluorosulfonyl)difluoroacetate.

19. A process for the production of trimethylsilyl (fluorosulfonyl)difluoroacetate, comprising: (a) contacting (fluorosulfonyl)difluoroacetyl fluoride with hexamethyldisiloxane to produce a mixture comprising trimethylsilyl (fluorosulfonyl)difluoroacetate and (fluorosulfonyl) difluoroacetic acid; (b) distilling said mixture in the presence of trimethylsilyl chloride to form a distillate comprising trimethylsilyl (fluorosulfonyl)difluoroacetate; and (c) recovering trimethylsilyl (fluorosulfonyl)difluoroacetate.

20. The process of claim 18 wherein said trimethylsilyl (fluorosulfonyl)difluoroacetate is recovered substantially free of (fluorosulfonyl)difluoroacetic acid.

21. The process of claim 19 wherein said trimethylsilyl (fluorosulfonyl)difluoroacetate is recovered substantially free of (fluorosulfonyl)difluoroacetic acid.

* * * * *